United States Patent
Spencer et al.

(10) Patent No.: US 9,534,070 B2
(45) Date of Patent: Jan. 3, 2017

(54) POLYMERIZATION PROCESSES FOR HIGH MOLECULAR WEIGHT POLYMERS

(71) Applicant: Dow Global Technologies LLC, Midland, MI (US)

(72) Inventors: Liam P. Spencer, Manvel, TX (US); Jennifer M. Kirschner, Lake Jackson, TX (US)

(73) Assignee: Dow Global Technologies LLC, Midland, MI (US)

( * ) Notice: Subject to any disclaimer, the term of this patent is extended or adjusted under 35 U.S.C. 154(b) by 0 days.

(21) Appl. No.: 14/443,663

(22) PCT Filed: Mar. 14, 2013

(86) PCT No.: PCT/US2013/031127
§ 371 (c)(1),
(2) Date: May 19, 2015

(65) Prior Publication Data
US 2015/0307643 A1 Oct. 29, 2015

Related U.S. Application Data

(60) Provisional application No. 61/753,962, filed on Jan. 18, 2013.

(51) Int. Cl.
| C08F 4/76 | (2006.01) |
|---|---|
| C08F 4/64 | (2006.01) |
| C08F 232/04 | (2006.01) |
| C08F 10/02 | (2006.01) |
| C07F 7/00 | (2006.01) |
| C08F 210/06 | (2006.01) |
| C08F 210/14 | (2006.01) |
| C08F 4/62 | (2006.01) |

(52) U.S. Cl.
CPC ............... *C08F 232/04* (2013.01); *C07F 7/00* (2013.01); *C08F 10/02* (2013.01); *C08F 210/06* (2013.01); *C08F 210/14* (2013.01); *C08F 4/62193* (2013.01); *C08F 4/64193* (2013.01)

(58) Field of Classification Search
CPC .................. C08F 4/64193; C08F 4/62193
See application file for complete search history.

(56) References Cited

U.S. PATENT DOCUMENTS

| 7,030,256 B2 * | 4/2006 | Boussie | ............... B01J 31/223 556/21 |
| 7,060,848 B2 * | 6/2006 | Boussie | ............... B01J 31/223 556/21 |
| 8,058,373 B2 * | 11/2011 | Stevens | ............... C08F 10/00 526/161 |
| 8,609,794 B2 * | 12/2013 | Klosin | ............... C08F 10/00 502/103 |
| 8,637,618 B2 * | 1/2014 | Diamond | ............... C08F 10/00 526/129 |
| 2011/0282018 A1 * | 11/2011 | Klosin | ............... C08F 10/00 526/170 |
| 2015/0291713 A1 * | 10/2015 | Klosin | ............... C08L 23/0815 526/170 |
| 2015/0322185 A1 | 11/2015 | Shan | |

FOREIGN PATENT DOCUMENTS

| WO | 2006/020624 A1 | 2/2006 |
| WO | 2007/136493 A2 | 11/2007 |
| WO | 2007/136494 A2 | 11/2007 |
| WO | 2007136495 A2 | 11/2007 |
| WO | 2007136496 A2 | 11/2007 |
| WO | 2007136497 A2 | 11/2007 |
| WO | 2007136506 A2 | 11/2007 |
| WO | 2009/067337 A1 | 5/2009 |
| WO | 2010/033601 A1 | 3/2010 |
| WO | 2010/078164 A1 | 7/2010 |
| WO | 2011/008837 A1 | 1/2011 |
| WO | 2011002986 A1 | 1/2011 |
| WO | 2011002998 A1 | 1/2011 |
| WO | 2012/004683 A2 | 1/2012 |
| WO | WO 2012/004683 A2 * | 1/2012 |

OTHER PUBLICATIONS

PCT/US2013/031127, International Search Report dated Jul. 24, 2014.
PCT/US2013/031127, International Preliminary Report on Patentability dated Jul. 21, 2015.
PCT/US2013/031127, Written Opinion of the International Searching Authority dated Jul. 18, 2015.

* cited by examiner

*Primary Examiner* — Rip A Lee

(57) ABSTRACT

A process to for polymerizing ethylene in the presence of a metal complex of Structure I, as described herein, which comprises a metal selected from one of Groups 3-6, which is bonded to aryl groups via oxygen and two Z groups. The aryl groups comprise substituents R1a, R1aa, through R15a, R15aa, which are selected from hydrogen, halo, hydrocarbyl, trihydrocarbylsilyl, trihydrocarbylsilylhydrocarbyl, —O(R), —N(R'R''), —S(R'''), or —P($R^{IV}R^V$); and each R, R', R'', R''', $R^{IV}$ and $R^V$ is described herein. Two X groups are also bonded to the metal, and each is halo, hydrocarbyl, or trihydrocarbylsilyl group. Each Z is O, S, N(C1-C40)hydrocarbyl, or P(C1-C40)hydrocarbyl. Groups Y and L form part of a bridge between the Z groups. Y is halo, hydrocarbyl, trihydrocarbylsilyl, trihydrocarbylsilylhydrocarbyl, —O($R^{VI}$), —N($R^{VII}R^{VIII}$), —S($R^{IX}$), or —P($R^XR^{XI}$); and each $R^{VI}$, $R^{VII}$, $R^{VIII}$, $R^{IX}$, $R^X$ and $R^{XI}$ is described herein. L is (C1-C40)hydrocarbylene or (C1-C40)heterohydrocarbylene. The invention also provides Structure I.

10 Claims, No Drawings

POLYMERIZATION PROCESSES FOR HIGH MOLECULAR WEIGHT POLYMERS

REFERENCE TO RELATED APPLICATIONS

This application claims the benefit of U.S. Provisional Application No. 61/753,962 filed on Jan. 18, 2013.

BACKGROUND

There is a need for new processes for the solution polymerization of high molecular weight ethylene-based polymers (for example, EPDM), using high polymerization temperatures (for example, greater than, or equal to, 160° C.). Conventional solution polymerizations are typically run at temperatures less than 160° C., and higher temperatures for the polymerization high molecular weight and high comonomer incorporation cannot be achieved, due to limitations with current polyolefin catalyst technology.

Some polyolefin polymerization processes and associated catalysts are described in the following references. International Publication WO2007/136497 discloses a catalyst composition comprising one or more metal complexes of a multifunctional Lewis base ligand, comprising a bulky, planar, aromatic- or substituted aromatic-group, and polymerization processes employing the same, for example, continuous, solution polymerization of one or more α-olefins at high catalyst efficiencies.

International Publication WO2007/136494 discloses a catalyst composition comprising a zirconium complex of a polyvalent aryloxyether. Such complex is used in a continuous solution polymerization of ethylene, one or more $C_{3-30}$ olefins, and a conjugated or nonconjugated diene, to prepare interpolymers having improved processing properties.

International Publication WO2007/136496 discloses metal complexes of polyvalent aryloxyethers, appropriately substituted with sterically bulky substituents that possess enhanced solubility in aliphatic and cycloaliphatic hydrocarbons. When such complexes are employed as catalyst components for the polymerization of ethylene/α-olefin copolymers, they produce products having reduced $I_{10}/I_2$ values.

International Publication WO2006/020624 discloses a supported, heterogeneous catalyst composition for use in the polymerization of addition polymerizable monomers, to form high molecular weight polymers. The catalyst composition comprises the following: 1) a substrate comprising a solid, particulated, high surface area, surface modified, inorganic oxide compound, 2) a Group 4 metal complex of a bis(hydroxyarylaryloxy) ligand; and optionally 3) an activating cocatalyst for the metal complex. International Publication WO2007/136493 discloses a process for the polymerization of propylene, optionally ethylene, and further, optionally, one or more $C_{4-30}$ α-olefins and/or one or more conjugated or nonconjugated dienes, under continuous, solution polymerization conditions, to prepare a high molecular weight polymer or interpolymer. The process comprising conducting the polymerization in the presence of a catalyst composition comprising a hafnium complex of a polyvalent aryloxyether.

International Publication WO2007/136495 discloses a catalyst composition comprising a zirconium complex of a polyvalent aryloxyether, and an alumoxane, and polymerization processes employing the same, and especially the continuous, solution polymerization of ethylene and one or more $C_{3-30}$ olefins or diolefins, to prepare copolymers having reduced cocatalyst by-product content. International Publication WO2007/136506 discloses a catalyst composition comprising a zirconium complex of a polyvalent aryloxyether, and a polymerization process employing the same, and especially a continuous, solution polymerization of ethylene and one or more $C_{3-30}$ olefins or diolefins, to prepare interpolymers having improved processing properties. See also the following references for polymerization processes, catalysts and/or polymer products: WO2011/002998, WO2011/002986, WO2009/067337, WO/2011/008837, and WO/2010/033601.

However, there remains a need for new polymerization processes that can be used to form high molecular weight ethylene-based polymers with good comonomer incorporation. There is a further need for such processes that can operate at higher temperatures (T>170° C.), enabling higher molecular weight polymers to be produced at lower, in-reactor viscosities. These needs have been met by the following invention.

SUMMARY OF INVENTION

The invention provides a process to form an ethylene-based polymer, said process comprising at least the following:

polymerizing ethylene in the presence of a metal complex selected from Structure I below:

(Structure I)

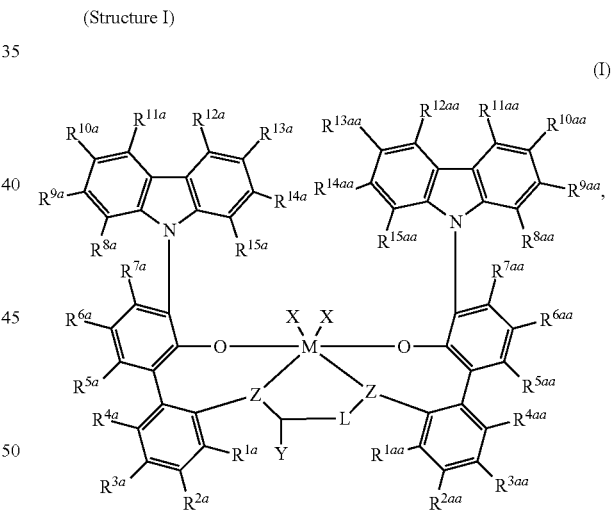

(I)

wherein:

M is a metal selected from Group 3, Group 4, Group 5 or Group 6 of the Periodic Table of the Elements;

R1a, R1aa, R2a, R2aa, R3a, R3aa, R4a, R4aa, R5a, R5aa, R6a, R6aa, R7a, R7aa, R8a, R8aa, R9a, R9aa, R10a, R10aa, R11a, R11aa, R12a, R12aa, R13a, R13aa, R14a, R14aa, R15a, R15aa, independently in each occurrence, is hydrogen, halo, hydrocarbyl, trihydrocarbylsilyl, trihydrocarbylsilylhydrocarbyl, —O(R), —N(R'R"), —S(R'"), or —P($R^{IV}R^V$); and wherein each R, R', R", R'", $R^{IV}$ and $R^V$ is independently hydrogen, a C1-C18 aliphatic hydrocarbyl, or a C1-C18 heterohydrocarbyl;

each X is independently selected from halo, hydrocarbyl, or trihydrocarbylsilyl group;

each Z is independently selected from O, S, N(C1-C40)hydrocarbyl, or P(C1-C40)hydrocarbyl;

Y is selected from halo, hydrocarbyl, trihydrocarbylsilyl, trihydrocarbylsilylhydrocarbyl, —O($R^{VI}$), —N($R^{VII}R^{VIII}$), —S($R^{IX}$), or —P($R^{X}R^{XI}$); and wherein each $R^{VI}$, $R^{VII}$, $R^{VIII}$, $R^{IX}$, $R^{X}$ and $R^{XI}$ is independently hydrogen, a C1-C18 aliphatic hydrocarbyl or a C1-C18 heterohydrocarbyl;

L is selected from (C1-C40)hydrocarbylene or (C1-C40)heterohydrocarbylene, and wherein the (C1-C40)heterohydrocarbylene comprises at least one heteroatom substituent, and wherein each heteroatom substituent is independently selected from the following: —O—, —S—, —S(O)—, —S(O)$_2$—, —Si($R^{XII}R^{XIII}$)—, —P($R^{XIV}$)—, —N($R^{XV}$)—; wherein each $R^{XII}$, $R^{XIII}$, $R^{XIV}$, $R^{XV}$ is independently hydrogen, a C1-C18 aliphatic hydrocarbyl, or a C1-C18 heterohydrocarbyl; or wherein each heteroatom substituent is independently selected from the following: —O($R^{XVI}$); —N($R^{XVII}R^{XVIII}$), —S($R^{XIX}$), or —P($R^{XX}R^{XXI}$); and wherein each $R^{XVI}$, $R^{XVII}$, $R^{XVIII}$; $R^{XIX}$, $R^{XX}$ and $R^{XXI}$ is independently hydrogen, a C1-C18 aliphatic hydrocarbyl, or a C1-C18 heterohydrocarbyl.

The invention also provides a metal complex selected from Structure I below:

(Structure I)

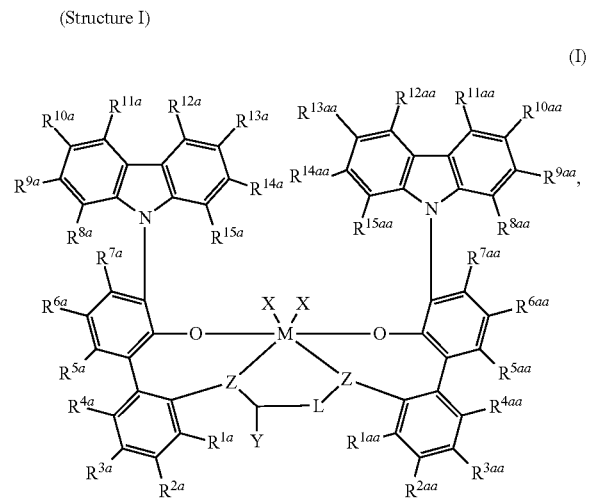

wherein the metal and substituents are described above.

(Structure I)

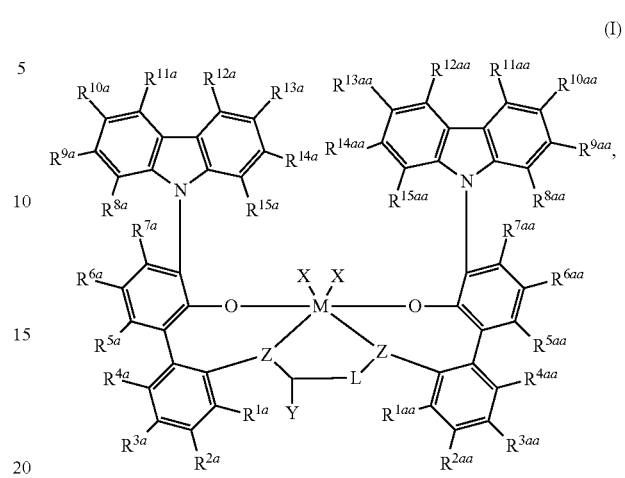

wherein the metal and substituents are described above.

An inventive process may comprise a combination of two or more embodiments as described herein.

In a second aspect, the invention provides a metal complex selected from Structure I below:

(Structure I)

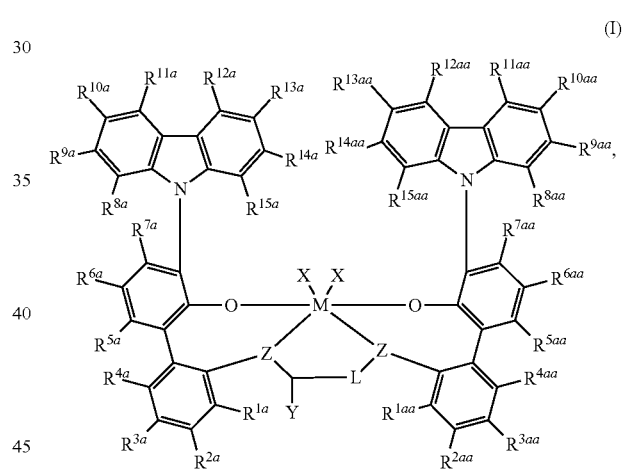

wherein the metal and substituents are described above.

An inventive metal complex may comprise a combination of two or more embodiments as described herein.

The following embodiments, directed to Structure I, apply to both aspects (process and metal complex) of the invention.

In one embodiment, for Structure I, R1a, R1aa, R2a, R2aa, R3a, R3aa, R4a, R4aa, R5a, R5aa, R6a, R6aa, R7a, R7aa, R8a, R8aa, R9a, R9aa, R10a, R10aa, R11a, R11aa, R12a, R12aa, R13a, R13aa, R14a, R14aa, R15a, R15aa, are each independently selected from hydrogen, halo, or hydrocarbyl. In a further embodiment, each is independently selected from hydrogen, halo, or (C1-C20)hydrocarbyl. In a further embodiment, each is independently selected from hydrogen, halo, or (C1-C6)hydrocarbyl.

In one embodiment, for Structure I, each Z is O.

In one embodiment, for Structure I, R6a and R6aa are each independently a ($C_4$-$C_{40}$)hydrocarbyl. In a further embodiment, R6a and R6aa are each independently a ($C_4$-$C_{20}$)hydrocarbyl. In a further embodiment, R6a and R6aa are each independently a ($C_4$-$C_8$)alkyl.

DETAILED DESCRIPTION OF THE INVENTION

New polymerization processes have been discovered that use certain bis-phenyl-phenoxy catalysts, and which offer the improvements in molecular weight with high comonomer incorporation, while maintaining high catalyst efficiency.

As discussed above, in a first aspect, the invention provides a process to form an ethylene-based polymer, said process comprising at least the following:

polymerizing ethylene in the presence of a metal complex selected from Structure I below:

In one embodiment, for Structure I, R10a, R13a, R10aa and R13aa, are each independently a $(C_1-C_{40})$hydrocarbyl. In a further embodiment, R10a, R13a, R10aa and R13aa are each independently a $(C_1-C_{20})$hydrocarbyl. In a further embodiment, R10a, R13a, R10aa and R13aa are each independently a $(C_4-C_8)$alkyl or phenyl.

In one embodiment, for Structure I, R3a and R3aa are each independently a $(C_1-C_6)$alkyl, a $(C_1-C_6)$alkyl-O—, a $((C_1-C_6)$alkyl$)_2$-N—, a $(C_3-C_6)$cycloalkyl, a fluorine atom, or a chlorine atom. In a further embodiment, R3a and R3aa are each independently a fluorine atom or a chlorine atom.

In one embodiment, for Structure I, R3a, R3aa, R10a, R13a, R10aa, R13aa, R6a and R6aa are not hydrogen atoms, and R3a and R3aa are the same as each other; R6a and R6aa are the same as each other; and R10a and R13a are respectively the same as R10aa and R13aa.

In one embodiment, each X is independently selected from halo, a (C1-C20)hydrocarbyl; or a trihydrocarbylsilyl group up to 20 atoms, not including hydrogen.

In one embodiment, each X is independently selected from halo, a (C1-C20)-hydrocarbyl, further a (C1-C10) hydrocarbyl, further a (C1-05)hydrocarbyl, and further a (C1-C3)hydrocarbyl.

In one embodiment, for Structure I, L is a $(C_1-C_{40})$ hydrocarbylene. In a further embodiment, L is a $(C_1-C_{20})$ hydrocarbylene, and further a $(C_1-C_{12})$hydrocarbylene.

In one embodiment, for Structure I, L is —CH$_2$CH$_2$CH$_2$—.

In one embodiment, for Structure I, M is a metal selected from Group 3, Group 4 or Group 5 of the Periodic Table of the Elements.

In one embodiment, for Structure I, M is a metal selected from Group 4 or Group 5 of the Periodic Table of the Elements.

In one embodiment, for Structure I, M is a metal selected from Group 4 of the Periodic Table of the Elements. In a further embodiment, the metal is Zr (zirconium), Ti (titanium) or Hf (hafnium). In a further embodiment, the metal is Zr or Hf. In a further embodiment, the metal is Hf. In a further embodiment, M is hafnium, and the hafnium is in a formal oxidation state of +4. In another embodiment, the metal is Zr.

In one embodiment, Structure I is selected from the following Structure II:

(Structure II)

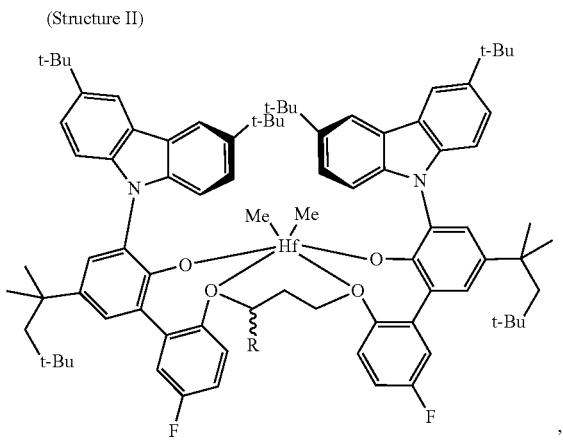

wherein R is a (C1-C8) alkyl group.

In one embodiment, for Structure II, R is selected from methyl, ethyl, n-propyl, iso-propyl, n-butyl, iso-butyl, or tert-butyl.

In one embodiment, Structure II is 6',6'''-(1-methyl-propane-1,3-diylbis(oxy))bis(3-(3,6-di-tert-butyl-9H-carbazol-9-yl)-3'-fluoro-5-(2,4,4-trimethylpentan-2-yl)-[1,1'-biphenyl]-2-ol)dimethyl-hafnium.

The metal complex may be activated to form an active catalyst composition by combination with one or more cocatalysts. Ionizing cocatalysts may contain an active proton, or some other cation associated with, but not coordinated to or only loosely coordinated to, an anion of the ionizing compound. Such compounds are described in European publications EP-A-570982, EP-A-520732, EP-A-495375, EP-A-500944, EP-A-277 003 and EP-A-277004, and U.S. Pat. Nos. 5,153,157, 5,198,401, 5,066,741, 5,206, 197, 5,241,025, 5,384,299 and 5,502,124. Preferred among the foregoing activators are ammonium cation containing salts, especially those containing trihydrocarbyl-substituted ammonium cations containing one or two $C_{10-40}$ alkyl groups, especially methylbis(octadecyl)-ammonium- and methylbis(tetradecyl)-ammonium-cations and a non-coordinating anion, especially a tetrakis(perfluoro)arylborate anion, especially tetrakis(pentafluorophenyl)borate. It is further understood that the cation may comprise a mixture of hydrocarbyl groups of differing lengths. For example, the protonated ammonium cation derived from a commercially available long-chain amine comprising a mixture of two $C_{14}$, $C_{16}$ or $C_{18}$ alkyl groups and one methyl group. Such amines are available from Chemtura Corp., under the trade name KEMAMINE T9701, and from Akzo-Nobel under the trade name ARMEEN M2HT. A most preferred ammonium salt activator is methyldi($C_{14-20}$ alkyl)ammonium tetrakis (pentafluorophenyl)borate.

Activation methods using ionizing ionic compounds not containing an active proton, but capable of forming active catalyst compositions, such as ferrocenium salts of the foregoing non-coordinating anions, are also contemplated for use herein, and are described in EP-A-426637, EP-A-573403 and U.S. Pat. No. 5,387,568. Also included is the use of strong Lewis acids, especially tris(perfluoro)aryl borane compounds, such as tris(pentafluoro-phenyl)borane, which are capable of abstraction of a ligand groups, especially a hydrocarbyl ligand, thereby forming a non-coordinating counter anion for the cationic derivative of the metal complex.

It is within the scope of this invention to use alumoxane(s) or modified alumoxane(s) as an activator or as a tertiary component in the invented process. That is, the compound may be used alone or in combination with other activators, either neutral or ionic, such as tri(alkyl)ammonium tetrakis (pentafluorophenyl)borate compounds, trisperfluoroaryl compounds, polyhalogenated heteroborane anions as disclosed in WO 98/43983, and combinations thereof. When used as a tertiary component, the amount of alumoxane employed is generally less than that necessary to effectively activate the metal complex when employed alone. In this embodiment, it is believed, without wishing to be bound by such belief, that the alumoxane does not contribute significantly to actual catalyst activation. Notwithstanding the foregoing, it is to be understood that some participation of the alumoxane in the activation process is not necessarily excluded.

The metal complex may be activated with a cation forming cocatalyst, a strong Lewis acid, or a combination thereof. Suitable cocatalysts include polymeric or oligomeric aluminoxanes, especially methyl aluminoxane, as well as inert, compatible, noncoordinating, ion forming compounds. So-called modified methyl aluminoxane (MMAO) or triethyl aluminum (TEA) are also suitable for use as a cocatalyst.

One technique for preparing such modified aluminoxane is disclosed in U.S. Pat. No. 5,041,584 (Crapo et al.). Aluminoxanes can also be made as disclosed in U.S. Pat. No. 5,542,199 (Lai et al.); U.S. Pat. No. 4,544,762 (Kaminsky et al.); U.S. Pat. No. 5,015,749 (Schmidt et al.); and U.S. Pat. No. 5,041,585.

In one embodiment, the process is a solution polymerization process. In a further embodiment, the polymerization is a continuous solution polymerization.

In one embodiment, the polymerization takes place at a polymerization temperature greater than, or equal to, 160° C.

In one embodiment, the polymerization takes place at a polymerization temperature from 160° C. to 220° C. In a further embodiment, the polymerization takes place at a polymerization temperature from 160° C. to 200° C.

In one embodiment, the polymerization takes place in at least one reactor.

In one embodiment, the polymerization takes place in at least two reactors.

In one embodiment, the polymerization takes place in at least two reactors in series.

In one embodiment, the polymerization takes place in at least two reactors. In a further embodiment, the second reactor temperature is greater than 160° C., and in a further embodiment, greater than 170° C.

In one embodiment, the polymerization takes place in at least two reactors in series. In a further embodiment, the second reactor temperature is greater than 160° C., and in a further embodiment, greater than 170° C.

In one embodiment, the first reactor temperature is from 160° C. to 200° C., and the second reactor temperature is from 150° C. to 200° C.

In one embodiment, the polymer concentration in each reactor is greater than 10 wt %, preferably greater than 15 wt %, and more preferably greater than 20 wt %, based on the total feed to reactor.

The invention also provides an olefin-based polymer formed from an inventive process of one or more embodiments described herein. In one embodiment, the olefin-based polymer is an ethylene-based polymer. In another embodiment, the olefin-based polymer is a propylene-based polymer.

The invention also provides an ethylene-based polymer formed from an inventive process of one or more embodiments described herein.

In one embodiment, the ethylene-based polymer has a rheology ratio (V0.1/V100 at 190° C.) greater than, or equal to, 30. In a further embodiment, the polymer has a rheology ratio (V0.1/V100 at 190° C.) greater than, or equal to, 40.

In one embodiment, the ethylene-based polymer has an Mw greater than 30,000 g/mole, further greater than, or equal to, 50,000 g/mole, further greater than, or equal to, 100,000 g/mole, further greater than, or equal to, 200,000 g/mole, and further greater than, or equal to, 300,000 g/mole. In a further embodiment, the ethylene-based polymer has a MWD (molecular weight distribution) from 1.5 to 3.0.

In one embodiment, the ethylene-based polymer has a MWD from 1.5 to 3.5, further from 1.7 to 3.0.

In one embodiment, the ethylene-based polymer has a Mw greater than 50,000 g/mole, and a MWD from 1.5 to 3.0.

In one embodiment, the ethylene-based polymer is a polyethylene homopolymer.

In one embodiment, the ethylene-based polymer is an ethylene-based interpolymer, and further an ethylene/α-olefin interpolymer, and further an ethylene/α-olefin copolymer.

In one embodiment, the interpolymer, and further the copolymer, has an "ethylene to α-olefin" molar ratio from 70/30 to 40/60.

In one embodiment, the interpolymer, and further the copolymer, has an "ethylene to α-olefin" molar ratio from 85/15 to 65/35.

In one embodiment, the interpolymer has a polyene weight percent content from 0.1 to 15 weight percent, preferably from 0.4 to 10 weight percent, based on the total weight of the interpolymer.

In one embodiment, the polymer is an ethylene/α-olefin/nonconjugated polyene interpolymer. In a further embodiment, the interpolymer is an ethylene/α-olefin/diene interpolymer. In a further embodiment, the interpolymer is an EPDM. In a further embodiment, the diene is ENB.

In one embodiment, the ethylene-based polymer has a "peak area from 21.3 ppm to 21.8 ppm" greater than 3.0 percent, further greater than, or equal to, 3.5 percent, further greater than, or equal to, 4.0 percent, of the total integral area from 19.5 ppm to 22.0 ppm, as determined by 13C NMR.

An olefin-based polymer may comprise a combination of two or more embodiments as described herein.

An ethylene-based polymer may comprise a combination of two or more embodiments as described herein.

A propylene-based polymer may comprise a combination of two or more embodiments as described herein.

The invention also provides a composition comprising an inventive olefin-based polymer of one or more embodiments described herein. In one embodiment, the olefin-based polymer is an ethylene-based polymer. In another embodiment, the olefin-based polymer is a propylene-based polymer.

The invention also provides a composition comprising an inventive ethylene-based polymer of one or more embodiments described herein.

The invention also provides an article comprising at least one component formed from an inventive composition.

An inventive composition may comprise a combination of two or more embodiments described herein.

An inventive process may comprise a combination of two or more embodiments described herein.

An inventive metal complex may comprise a combination of two or more embodiments described herein.

An inventive article may comprise a combination of two or more embodiments described herein.

Ethylene/α-Olefin Interpolymer

In one embodiment, the ethylene-based polymer is an ethylene/α-olefin interpolymer. Ethylene/α-olefin interpolymers include polymers formed by polymerizing ethylene with one or more, and preferably one, C3-C10 α-olefin(s). Illustrative α-olefins include propylene, 1-butene, 1-pentene, 1-hexene, 4-methyl-1-pentene, 1-heptene, 1-octene, 1-nonene and 1-decene. Preferably, the α-olefin is propylene, 1-butene, 1-hexene or 1-octene. Preferred copolymers include ethylene/propylene (EP) copolymers, ethylene/butene (EB) copolymers, ethylene/hexene (EH) copolymers, ethylene/octene (EO) copolymers.

In one embodiment, the ethylene/α-olefin interpolymer has a density greater than, or equal to, 0.850 g/cc, or greater than, or equal to, 0.855 g/cc, or greater than, or equal to, 0.860 g/cc. In a further embodiment, the ethylene/α-olefin interpolymer is an ethylene/α-olefin copolymer.

In one embodiment, the ethylene/α-olefin interpolymer has a density less than, or equal to, 0.900 g/cc, or less than, or equal to, 0.895 g/cc, or less than, or equal to, 0.890 g/cc. In a further embodiment, the ethylene/α-olefin interpolymer is an ethylene/α-olefin copolymer.

In one embodiment, the ethylene/α-olefin interpolymer has a melt index (I2) greater than 0.1 g/10 min, or greater than, or equal to, 0.5 g/10 min, or greater than, or equal to, 1.0 g/10 min. In a further embodiment, the ethylene/α-olefin interpolymer is an ethylene/α-olefin copolymer.

In one embodiment, the ethylene/α-olefin interpolymer has a melt index (I2) greater than 2.0 g/10 min, or greater than, or equal to, 3.0 g/10 min, or greater than, or equal to, 5.0 g/10 min. In a further embodiment, the ethylene/α-olefin interpolymer is an ethylene/α-olefin copolymer.

In one embodiment, the ethylene/α-olefin interpolymer has a melt index (I2) greater than 10 g/10 min, or greater than, or equal to, 15 g/10 min, or greater than, or equal to, 20 g/10 min. In a further embodiment, the ethylene/α-olefin interpolymer is an ethylene/α-olefin copolymer.

In one embodiment, the ethylene/α-olefin interpolymer has a melt index (I2) less than, or equal to, 500 g/10 min, or less than, or equal to, 200 g/10 min, or less than, or equal to, 100 g/10 min, or less than, or equal to, 50 g/10 min. In a further embodiment, the ethylene/α-olefin interpolymer is an ethylene/α-olefin copolymer.

In one embodiment, the ethylene/α-olefin interpolymer has molecular weight distribution (Mw/Mn) greater than, or equal to, 1.1, or greater than, or equal to, 1.2, or greater than, or equal to, 1.5, or greater than, or equal to, 1.7, as determined by GPC. In a further embodiment, the ethylene/α-olefin interpolymer is an ethylene/α-olefin copolymer.

In one embodiment, the ethylene/α-olefin interpolymer has molecular weight distribution (Mw/Mn) less than, or equal to, 4.0, or less than, or equal to, 3.5, or less than, or equal to, 3.0, or less than, or equal to, 2.5, as determined by GPC. In a further embodiment, the ethylene/α-olefin interpolymer is an ethylene/α-olefin copolymer.

In one embodiment, the ethylene/α-olefin interpolymer is a homogeneously branched linear interpolymer, and preferably a copolymer, or a homogeneous branched substantially linear interpolymer, and preferably a copolymer.

In one embodiment, the ethylene/α-olefin interpolymer is a homogeneous branched substantially linear interpolymer, and preferably a copolymer.

In one embodiment, the ethylene/α-olefin interpolymer is a homogeneous branched linear interpolymer, and preferably a copolymer.

The terms "homogeneous" and "homogeneously-branched" are used in reference to an ethylene/α-olefin interpolymer, in which the α-olefin comonomer is randomly distributed within a given polymer molecule, and all of the polymer molecules have the same or substantially the same comonomer-to-ethylene ratio.

The homogeneously branched linear ethylene interpolymers are ethylene polymers, which lack long chain branching, but do have short chain branches, derived from the comonomer polymerized into the interpolymer, and which are homogeneously distributed, both within the same polymer chain, and between different polymer chains. These ethylene/α-olefin interpolymers have a linear polymer backbone, no measurable long chain branching, and a narrow molecular weight distribution. This class of polymers is disclosed, for example, by Elston in U.S. Pat. No. 3,645,992, and subsequent processes to produce such polymers, using bis-metallocene catalysts, have been developed, as shown, for example, in EP 0 129 368; EP 0 260 999; U.S. Pat. Nos. 4,701,432; 4,937,301; 4,935,397; 5,055,438; and WO 90/07526; each incorporated herein by reference. As discussed, the homogeneously branched linear ethylene interpolymers lack long chain branching, just as is the case for the linear low density polyethylene polymers or linear high density polyethylene polymers.

The homogeneously branched substantially linear ethylene/α-olefin interpolymers are described in U.S. Pat. Nos. 5,272,236; 5,278,272; 6,054,544; 6,335,410 and 6,723,810; each incorporated herein by reference. The substantially linear ethylene/α-olefin interpolymers have long chain branching. The long chain branches have the same comonomer distribution as the polymer backbone, and can have about the same length as the length of the polymer backbone. "Substantially linear," typically, is in reference to a polymer that is substituted, on average, with "0.01 long chain branches per 1000 carbons" to "3 long chain branches per 1000 carbons." The length of a long chain branch is longer than the carbon length of a short chain branch, formed from the incorporation of one comonomer into the polymer backbone.

The substantially linear ethylene/α-olefin interpolymers form a unique class of homogeneously branched ethylene polymers. They differ substantially from the well-known class of conventional, homogeneously branched linear ethylene/α-olefin interpolymers, as discussed above, and, moreover, they are not in the same class as conventional heterogeneous "Ziegler-Natta catalyst polymerized" linear ethylene polymers (for example, ultra low density polyethylene (ULDPE), linear low density polyethylene (LLDPE) or high density polyethylene (HDPE), made, for example, using the technique disclosed by Anderson et al., in U.S. Pat. No. 4,076,698); nor are they in the same class as high pressure, free-radical initiated, highly branched polyethylenes, such as, for example, low density polyethylene (LDPE), ethylene-acrylic acid (EAA) copolymers and ethylene vinyl acetate (EVA) copolymers.

The homogeneously branched, substantially linear ethylene/α-olefin interpolymers useful in the invention have excellent processability, even though they have a relatively narrow molecular weight distribution. Surprisingly, the melt flow ratio (I10/I2), according to ASTM D 1238, of the substantially linear ethylene interpolymers can be varied widely, and essentially independently of the molecular weight distribution (Mw/Mn or MWD). This surprising behavior is contrary to conventional homogeneously branched linear ethylene interpolymers, such as those described, for example, by Elston in U.S. Pat. No. 3,645,992, and heterogeneously branched, conventional "Ziegler-Natta polymerized," linear polyethylene interpolymers, such as those described, for example, by Anderson et al., in U.S. Pat. No. 4,076,698. Unlike substantially linear ethylene interpolymers, linear ethylene interpolymers (whether homogeneously or heterogeneously branched) have rheological properties, such that, as the molecular weight distribution increases, the I10/I2 value also increases.

Long chain branching can be determined by using 13C Nuclear Magnetic Resonance (NMR) spectroscopy, and can be quantified using the method of Randall (Rev. Macromol. Chem. Phys., C29 (2 &3), 1989, p. 285-297), the disclosure of which is incorporated herein by reference. Two other methods are Gel Permeation Chromatography, couple with a Low Angle Laser Light Scattering detector (GPCLALLS), and Gel Permeation Chromatography, coupled with a Differential Viscometer detector (GPC-DV). The use of these techniques for long chain branch detection, and the underlying theories, have been well documented in the literature. See, for example, Zimm, B H and Stockmayer, W. H., J.

Chem. Phys., 17, 1301(1949), and Rudin, A., Modern Methods of Polymer Characterization, John Wiley & Sons, New York (1991) pp. 103-112.

In contrast to "substantially linear ethylene polymer," "linear ethylene polymer" means that the polymer lacks measurable or demonstrable long chain branches, that is, the polymer is substituted with an average of less than "0.01 long chain branch per 1000 carbons."

In one embodiment, the ethylene/α-olefin interpolymer has a PRR (Processing Rheology Ratio) greater than, or equal to, 4.0, or greater than, or equal to, 8.0, or greater than, or equal to, 12, or greater than, or equal to, 15. In a further embodiment, the ethylene/α-olefin interpolymer is an ethylene/α-olefin copolymer.

In one embodiment, the ethylene/α-olefin interpolymer has a PRR from 4.0 to 70, or from 8.0 to 65, or from 12 to 60. In a further embodiment, the ethylene/α-olefin interpolymer is an ethylene/α-olefin copolymer.

Interpolymer viscosity is conveniently measured in poise (dyne-second/square centimeter (d-sec/cm$^2$)) at shear rates within a range of 0.1-100 radian per second (rad/sec), at 190° C., under a nitrogen atmosphere, using a dynamic mechanical spectrometer (such as a RMS-800 or ARES from Rheometrics), under a dynamic sweep made from 0.1 to 100 rad/sec. The viscosities at "0.1 rad/sec" and "100 rad/sec" may be represented, respectively, as "V0.1" and "V100," with a ratio of the two referred to as "RR," and expressed as "V0.1/V100."

The PRR value is calculated by the formula: PRR=RR+[3.82−interpolymer Mooney Viscosity (ML1+4 at 125° C.)]×0.3. The PRR determination is described in U.S. Pat. No. 6,680,361 (see also equivalent WO 00/26268), fully incorporated herein by reference.

An ethylene/α-olefin interpolymer may comprise a combination of two or more embodiments as described herein.

An ethylene/α-olefin copolymer may comprise a combination of two or more embodiments as described herein.

Ethylene/α-Olefin/Nonconjugated Polyene Interpolymer

In one embodiment, the ethylene-based polymer is an ethylene/α-olefin/-nonconjugated polyene interpolymer. In a further embodiment, the ethylene/α-olefin/nonconjugated polyene interpolymer is an ethylene/α-olefin/dene interpolymer. In a further embodiment, the interpolymer is an EPDM. In a further embodiment, the diene is ENB.

The ethylene/α-olefin/nonconjugated polyene interpolymers comprise, in polymerize form, ethylene, an α-olefin, and a nonconjugated polyene. Suitable examples of α-olefins include the C3-C10 α-olefins, and preferably propylene. Suitable examples of nonconjugated polyenes include the C4-C40 nonconjugated dienes.

The α-olefin may be either an aliphatic or an aromatic compound. The α-olefin is preferably a C3-C20 aliphatic compound, preferably a C3-C16 aliphatic compound, and more preferably a C3-C10 aliphatic compound. Preferred C3-C10 aliphatic α-olefins are selected from the group consisting of propylene, 1-butene, 1-hexene and 1-octene, and more preferably propylene.

Illustrative nonconjugated polyenes include straight chain acyclic dienes, such as 1,4-hexadiene and 1,5-heptadiene; branched chain acyclic dienes, such as 5-methyl-1,4-hexadiene, 2-methyl-1,5-hexadiene, 6-methyl-1,5-heptadiene, 7-methyl-1,6-octadiene, 3,7-dimethyl-1,6-octadiene, 3,7-dimethyl-1,7-octadiene, 5,7-dimethyl-1,7-octadiene, 1,9-decadiene, and mixed isomers of dihydromycene; single ring alicyclic dienes such as 1,4-cyclohexadiene, 1,5-cyclooctadiene and 1,5-cyclododecadiene; multi-ring alicyclic fused and bridged ring dienes, such as tetrahydroindene, methyl tetrahydroindene; alkenyl, alkylidene, cycloalkenyl and cycloalkylidene norbornenes such as 5-methylene-2-norbornene (MNB), 5-ethylidene-2-norbornene (ENB), 5-vinyl-2-norbornene, 5-propenyl-2-norbornene, 5-isopropylidene-2-norbornene, 5-(4-cyclopentenyl)-2-norbornene, and 5-cyclohexylidene-2-norbornene. The diene is preferably a nonconjugated diene selected from the group consisting of ENB, dicyclopentadiene, 1,4-hexadiene, 7-methyl-1,6-octadiene, and preferably, ENB, dicyclopentadiene and 1,4-hexadiene, more preferably ENB and dicyclopentadiene, and even more preferably ENB.

In one embodiment, the ethylene/α-olefin/nonconjugated polyene interpolymer comprises a majority amount of polymerized ethylene, based on the weight of the interpolymer. In a further embodiment, the ethylene/α-olefin/nonconjugated polyene interpolymer is an ethylene/α-olefin/dene interpolymer. In a further embodiment, the interpolymer is an EPDM. In a further embodiment, the diene is ENB.

In one embodiment, the ethylene/α-olefin/nonconjugated polyene interpolymer has a molecular weight distribution (Mw/Mn) from 1.5 to 3.5, further from 1.8 to 3.0, further from 2.0 to 2.6. In a further embodiment, the ethylene/α-olefin/nonconjugated polyene interpolymer is an ethylene/α-olefin/dene interpolymer. In a further embodiment, the interpolymer is an EPDM. In a further embodiment, the diene is ENB.

In one embodiment, the ethylene/α-olefin/nonconjugated polyene interpolymer has an "ethylene to α-olefin" molar ratio from 85/15 to 40/60. In a further embodiment, the interpolymer is an EPDM. In a further embodiment, the diene is ENB.

In one embodiment, the ethylene/α-olefin/nonconjugated polyene interpolymer has an "ethylene to α-olefin" molar ratio from 85/15 to 65/35. In a further embodiment, the interpolymer is an EPDM. In a further embodiment, the diene is ENB.

In one embodiment, the interpolymer has a polyene weight percent content from 0.1 to 15 weight percent, preferably from 0.4 to 10 weight percent, based on the total weight of the interpolymer. In a further embodiment, the interpolymer is an EPDM. In a further embodiment, the diene is ENB.

In one embodiment, the ethylene/α-olefin/nonconjugated polyene interpolymer has a "peak area from 21.3 ppm to 21.8 ppm" greater than 3.0 percent of the total integral area from 19.5 ppm to 22.0 ppm, as determined by 13C NMR. In a further embodiment, the interpolymer is an EPDM. In a further embodiment, the diene is ENB.

In one embodiment, the ethylene/α-olefin/nonconjugated polyene interpolymer has a "peak area from 21.3 ppm to 21.8 ppm" greater than, or equal to, 3.5 percent, further greater than, or equal to, 4.0 weight percent, further greater than, or equal to, 5.0 weight percent, and further greater than, or equal to, 6.0 weight percent, of the total integral area from 19.5 ppm to 22.0 ppm, as determined by 13C NMR. In a further embodiment, the interpolymer is an EPDM. In a further embodiment, the diene is ENB.

An inventive ethylene/α-olefin/nonconjugated polyene interpolymer may comprise a combination of two or more embodiments as described herein.

An ethylene/alpha-olefin/diene interpolymer may comprise a combination of two or more embodiments as described herein.

An EPDM terpolymer may comprise a combination of two or more embodiments as described herein.

Additives

An inventive composition may comprise one or more additives. Suitable additives include, but are not limited to, fillers, antioxidants, UV stabilizers, flame retardants, plasticizers or oils, crosslinking agents, colorants or pigments, and combinations thereof.

Fillers include, but are not limited to, carbon black; silicates of aluminum, magnesium, calcium, sodium, potassium and mixtures thereof; carbonates of calcium, magnesium and mixtures thereof; oxides of silicon, calcium, zinc, iron, titanium, and aluminum; sulfates of calcium, barium, and lead; alumina trihydrate; magnesium hydroxide; phenol-formaldehyde, polystyrene, and poly(alphamethyl)-styrene resins, natural fibers, synthetic fibers, and the like.

Plasticizers include, but are not limited to, petroleum oils, such as aromatic and naphthenic oils; polyalkylbenzene oils; organic acid monoesters, such as alkyl and alkoxyalkyl oleates and stearates; organic acid diesters, such as dialkyl, dialkoxyalkyl, and alkyl aryl phthalates, terephthalates, sebacates, adipates, and glutarates; glycol diesters, such as tri-, tetra-, and polyethylene glycol dialkanoates; trialkyl trimellitates; trialkyl, trialkoxyalkyl, alkyl diaryl, and triaryl phosphates; chlorinated paraffin oils; coumarone-indene resins; pine tars; vegetable oils, such as castor, tall, rapeseed, and soybean oils and esters and epoxidized derivatives thereof; and the like.

Antioxidants include, but are not limited to, hindered phenols, bisphenols, and thiobisphenols; substituted hydroquinones; tris(alkylphenyl)phosphites; dialkylthiodipropionates; phenylnaphthylamines; substituted diphenylamines; dialkyl, alkyl aryl, and diaryl substituted p-phenylene diamines; monomeric and polymeric dihydroquinolines; 2-(4-hydroxy-3,5-t-butylaniline)-4,6-bis(octylthio)1,3,5-triazine, hexahydro-1,3,5-tris-β-(3,5-di-t-butyl-4-hydroxyphenyl)propionyl-s-triazine, 2,4,6-tris(n-1,4-dimethylpentyl-phenylene-diamino)-1,3,5-triazine, tris-(3,5-di-t-butyl-4-hydroxybenzyl)-isocyanurate, nickel dibutyldithiocarbamate, 2-mercaptotolylimidazole and its zinc salt, petroleum waxes, and the like.

Crosslinking agents include, but are not limited to, peroxides, such as organic peroxides. Illustrative peroxides include, but are not limited to, a series of vulcanizing and polymerization agents that contain α,α'-bis(t-butylperoxy)-diisopropylbenzene, and are available from Hercules, Inc. under the trade designation VULCUP, a series of such agents that contain dicumyl peroxide and are available from Hercules, Inc. under the trade designation DI-CUP as well as LUPERSOL peroxides made by Elf Atochem, North America or TRIGONOX organic peroxides made by Akzo Nobel. The LUPERSOL peroxides include LUPERSOL 101 (2,5-dimethyl-2,5-di(t-butylperoxy)hexane), LUPERSOL 130 (2,5-dimethyl-2,5-di(t-butylperoxy)hexyne-3) and LUPERSOL 575 (t-amyl peroxy-2-ethylhexonate). Other suitable peroxides include 2,5-dimethyl-2,5-di-(t-butyl peroxy)hexane, di-t-butylperoxide, di-(t-amyl)peroxide, 2,5-di (t-amyl peroxy)-2,5-dimethylhexane, 2,5-di-(t-butylperoxy)-2,5-diphenylhexane, bis(alpha-methylbenzyl) peroxide, benzoyl peroxide, t-butyl perbenzoate, 3,6,9-triethyl-3,6,9-trimethyl-1,4,7-triperoxonane and bis(t-butylperoxy)-diisopropylbenzene.

In one embodiment, the composition further comprises at least one oil. In a further embodiment, the oil is present in an amount greater than 10 weight percent, or greater than 15 weight percent, or greater than 20 weight percent, based on the weight of the composition.

In one embodiment, the oil is present in an amount less than 60 weight percent, or less than 50 weight percent, or less than 40 weight percent, based on the weight of the composition.

Applications

The compositions of the present invention may be used to prepare a variety of articles, or their component parts or portions. The inventive compositions may be converted into a finished article of manufacture by any one of a number of conventional processes and apparatus. Illustrative processes include, but are not limited to, extrusion, calendering, compression molding, and other typical thermoset material forming processes. For example, articles can be prepared by extrusion, extrusion followed by additional thermal treatment, low pressure molding, compression molding, and the like.

Articles include, but are not limited to, sheets, foams, molded goods, and extruded parts. Additional articles include automotive parts, weather strips, belts, hoses, building profiles, wire and cable jacketing, flooring materials, gaskets, tires and tire components, computer parts, building materials and footwear components. A skilled artisan can readily augment this list without undue experimentation.

Definitions

Unless stated to the contrary, implicit from the context, or customary in the art, all parts and percents are based on weight, and all test methods are current as of the filing date of this disclosure.

A continuous polymerization process is a process conducted at steady-state, with continuous feeds and continuous removal of product. Such processes include, but are not limited to, one or more well-mixed loop reactor(s) and/or stirred tank reactor(s) and/or plug-flow reactors, and where multiple reactors can be operated in sequence and/or in parallel.

A batch process is a process conducted in a batch-wise fashion, such as the reactants and monomers are added once, and then partially or totally consumed during the reaction. Batch reactors are operated at non-steady states, since the reactants are consumed with time.

A semi-batch process is operated with both continuous and batch inputs and outputs. One chemical reactant is charged to the reactor vessel, and a second chemical is added slowly. For example, ethylene and propylene are fed continuously to a polymerization, while the solvent and termonomer are added only at the beginning of the reaction. Semi-batch reactors are operated at non-steady states, since some of the reactants are consumed with time.

The term "hydrocarbyl," as used herein refers to a univalent group containing only carbon and hydrogen atoms, for example —CH2CH3. A hydrocarbyl can be aliphatic (linear or branched) or aromatic.

The term "hydrocarbylene," as used herein refers to a bivalent group containing only carbon and hydrogen atoms, for example, —CH2CH2-. A hydrocarbylene can be aliphatic (linear or branched) or aromatic.

The term "heterohydrocarbyl," as used herein, refers to a hydrocarbyl comprising at least one heteroatom substituent. A heteroatom substituent comprises at least one heteroatom, and may comprise hydrogen and/or carbon. Examples of heteroatoms include, for example, O, N, S and P.

The term "heterohydrocarbylene," as used herein, refers to a hydrocarbylene comprising at least one heteroatom substituent. A heteroatom substituent comprises at least one heteroatom, and may comprise hydrogen and/or carbon. Examples of heteroatoms include, for example, O, N, S and P.

The term "composition," as used herein, includes the material(s) which comprise the composition, as well as reaction products and decomposition products formed from the materials of the composition. Any reaction product or decomposition product is typically present in trace or residual amounts.

The term "polymer," as used herein, refers to a polymeric compound prepared by polymerizing monomers, whether of the same or a different type. The generic term polymer thus embraces the term homopolymer (employed to refer to polymers prepared from only one type of monomer, with the understanding that trace amounts of impurities can be incorporated into the polymer structure) and the term interpolymer as defined hereinafter. Trace amounts of impurities, for example, catalyst residues, may be incorporated into and/or within the polymer.

The term "interpolymer," as used herein, refers to polymers prepared by the polymerization of at least two different types of monomers. The term interpolymer thus includes the term copolymer (employed to refer to polymers prepared from two different types of monomers) and polymers prepared from more than two different types of monomers.

The term "ethylene-based polymer," as used herein, refers to a polymer that comprises, in polymerized form, a majority amount of ethylene (based on the weight of the polymer), and optionally may comprise one or more comonomers.

The term "ethylene-based interpolymer," as used herein, refers to a polymer that comprises, in polymerized form, a majority amount of ethylene (based on the weight of the interpolymer), and at least one comonomer.

The term "ethylene/α-olefin/nonconjugated polyene interpolymer," as used herein, refers to a polymer that comprises, in polymerized form, ethylene, an α-olefin, and a nonconjugated polyene. In one embodiment, the "ethylene/α-olefin/nonconjugated polyene interpolymer" comprises a majority amount of ethylene (based on the weight of the interpolymer).

The term "ethylene/α-olefin/diene interpolymer," as used herein, refers to a polymer that comprises, in polymerized form, ethylene, an α-olefin, and a diene. In one embodiment, the "ethylene/α-olefin/diene interpolymer" comprises a majority amount of ethylene (based on the weight of the interpolymer).

The term, "ethylene/α-olefin interpolymer," as used herein, refers to an interpolymer that comprises, in polymerized form, a majority amount of ethylene monomer (based on the weight of the interpolymer), and an α-olefin.

The term, "ethylene/α-olefin copolymer," as used herein, refers to a copolymer that comprises, in polymerized form, a majority amount of ethylene monomer (based on the weight of the copolymer), and an α-olefin, as the only two monomer types.

The term "propylene-based polymer," as used herein, refers to a polymer that comprises, in polymerized form, a majority amount of propylene (based on the weight of the polymer), and optionally may comprise one or more comonomers.

The term "propylene-based interpolymer," as used herein, refers to a polymer that comprises, in polymerized form, a majority amount of propylene (based on the weight of the interpolymer), and at least one comonomer.

The term, "propylene/α-olefin interpolymer," as used herein, refers to an interpolymer that comprises, in polymerized form, a majority amount of propylene monomer (based on the weight of the interpolymer), and an α-olefin.

The term, "propylene/α-olefin copolymer," as used herein, refers to a copolymer that comprises, in polymerized form, a majority amount of propylene monomer (based on the weight of the copolymer), and an α-olefin, as the only two monomer types.

The term, "propylene/ethylene interpolymer," as used herein, refers to an interpolymer that comprises, in polymerized form, a majority amount of propylene monomer (based on the weight of the interpolymer), and ethylene.

The term, "propylene/ethylene copolymer," as used herein, refers to a copolymer that comprises, in polymerized form, a majority amount of propylene monomer (based on the weight of the copolymer), and ethylene, as the only two monomer types.

The terms "comprising," "including," "having," and their derivatives, are not intended to exclude the presence of any additional component, step or procedure, whether or not the same is specifically disclosed. In order to avoid any doubt, all compositions claimed through use of the term "comprising" may include any additional additive, adjuvant, or compound, whether polymeric or otherwise, unless stated to the contrary. In contrast, the term, "consisting essentially of" excludes from the scope of any succeeding recitation any other component, step or procedure, excepting those that are not essential to operability. The term "consisting of" excludes any component, step or procedure not specifically delineated or listed.

Test Methods

Density—Density is measured in accordance with ASTM D-792.

Melt Index—Melt index (I2, or MI) of an ethylene-based polymer is measured in accordance with ASTM D-1238, condition 190° C./2.16 kg. Melt flow rate (MFR) of an propylene-based polymer is measured in accordance with ASTM D-1238, condition 230° C./2.16 kg.

FTIR Method for Polymer Composition Analysis

Polymers containing ethylene, propylene, octene, and/or ENB were analyzed using ASTM D9300 for ethylene content, and ASTM D6047 for its α-olefin and/or ENB content.

The polymer samples were dissolved in 1,2,4-trichlorobenzene stabilized with butylated hydroxytoluene. The samples were heated to 160° C., and shaken for approximately one hour to completely dissolve the polymer. An aliquot of the polymer was deposited into a sample well on an arrayed silicon IR wafer. The arrayed wafer was held at 140° C. for at least 30 minutes, and then slowly cooled to room temperature. The deposited sample was then analyzed on a nitrogen-sparged FTIR spectrometer, to determine the weight percentage of one or more of ethylene, propylene, 1-octene, and/or ENB, in the polymer (wt % of each monomer based on weight of polymer).

Gel Permeation Chromatography

The chromatographic system consisted of either a Polymer Laboratories Model PL-210 or a Polymer Laboratories Model PL-220. The column and carousel compartments were operated at 140° C. The columns were three Polymer Laboratories, 10-micron, Mixed-B columns. The solvent was 1,2,4 trichlorobenzene. The samples were prepared at a concentration of "0.1 gram of polymer in 50 milliliters of solvent." The solvent used to prepare the samples contained "200 ppm of butylated hydroxytoluene (BHT)." Samples were prepared by agitating lightly for two hours at 160° C. The injection volume was 100 microliters, and the flow rate was 1.0 milliliters/minute.

Calibration of the GPC column set was performed with 21 narrow molecular weight distribution polystyrene standards, with molecular weights ranging from 580 to 8,400,000, arranged in six "cocktail" mixtures, with at least a decade of separation between individual molecular weights. The standards were purchased from Polymer Laboratories (Shropshire, UK). The polystyrene standards were prepared at "0.025 grams in 50 milliliters of solvent" for molecular weights equal to, or greater than, 1,000 kg/mol, and "0.05 grams in 50 milliliters of solvent" for molecular weights less than 1,000 kg/mol. The polystyrene standards were dissolved at 80 degrees Celsius, with gentle agitation, for 30 minutes. The dissolved standards were run first, and in order of decreasing highest molecular weight component to minimize degradation. The polystyrene standard peak molecular weights were converted to polyethylene molecular weights using the following equation, $M_{polyethylene} = A \times (M_{polystyrene})^B$, where M is the molecular weight, A has a value of 0.431 and B is equal to 1.0. Polyethylene equivalent molecular weight calculations were performed using VISCOTEK TriSEC software Version 3.0.

Experimental

I. Catalysts

The catalysts used in this study are shown below.

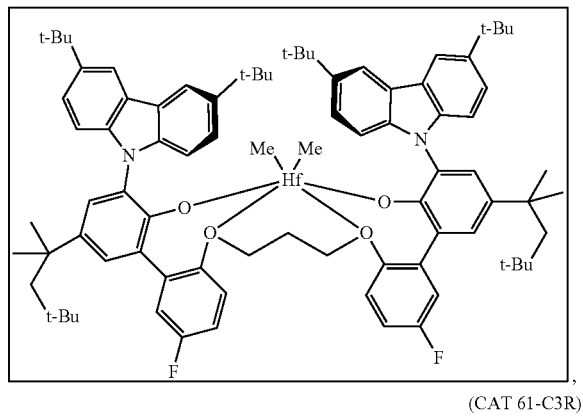

(CAT 61)

(CAT 61-C3R)

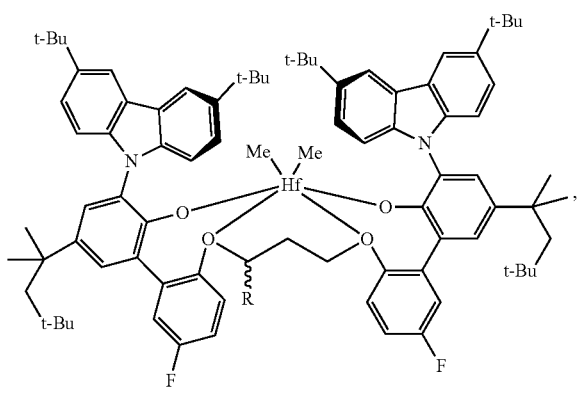

R = Me, Et, $^n$Pr, $^i$Pr, $^n$Bu, $^i$Bu, $^t$Bu

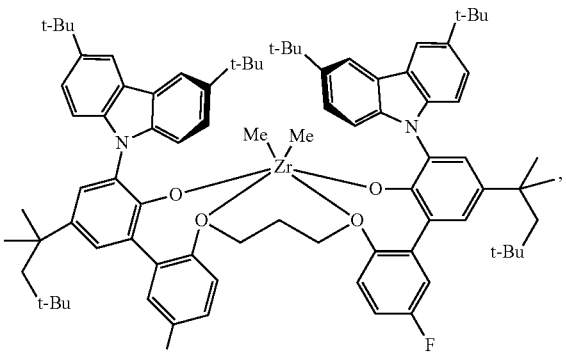

(CAT 54)

(CAT 61-C3R-Zr)

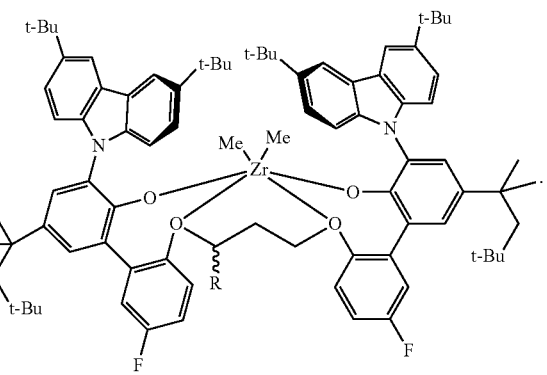

R = Me, Et, $^n$Pr, $^i$Pr, $^n$Bu, $^i$Bu, $^t$Bu

II. Catalyst Synthesis

Overview—Representative

The synthesis of the ligand and subsequent catalyst structure, which possesses one R substituent at the α-position on a three carbon ether bridge, required the preparation of an appropriately substituted "bottom fragment" and "top fragment." These molecules were coupled together utilizing Suzuki coupling conditions (below) to produce the desired biphenylphenol ligand. For example, the desired top fragments can be synthesized following known procedures such as those described in WO 2003/091262 and WO 2007/136494. These derivatives can be coupled following similar procedures, like those described in WO 2003/091262 and WO 2007/136494 with suitable bottom fragments. Coupling of the two fragments produced the C1-symmetric biphenylphenol ligands, which were subsequently metallated with a Group IV metal (e.g., hafnium or zirconium) to produce the desired catalyst compounds. The metallation and Suzuki couplings steps were similar to those previously described by in WO2003/091262 and WO 2007/136494.

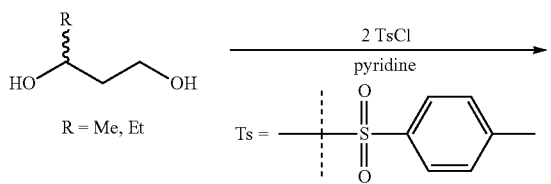

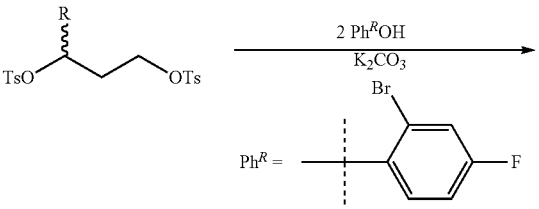

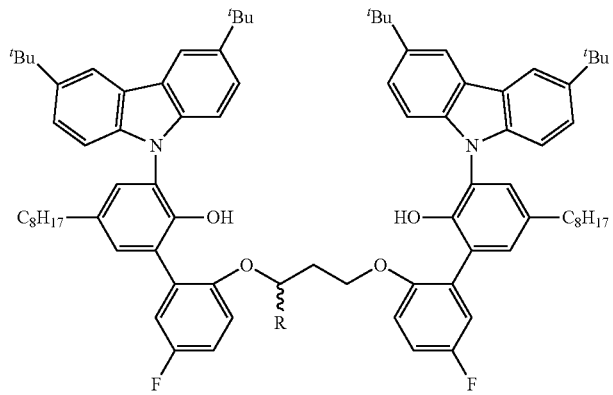
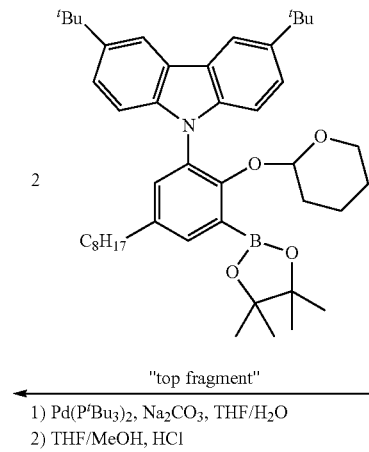
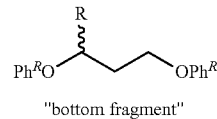

"bottom fragment"

"top fragment"

1) Pd(P'Bu₃)₂, Na₂CO₃, THF/H₂O
2) THF/MeOH, HCl

CAT 61-C3Me-Hf

The 6',6'''-(1-methyl-propane-1,3-diylbis(oxy))bis(3-(3,6-di-tert-butyl-9H-carbazol-9-yl)-3'-fluoro-5-(2,4,4-trimethyl-pentan-2-yl)-[1,1'-biphenyl]-2-ol) (0.810 g, 0.65 mmol) and HfCl4 (0.209 g, 0.65 mmol) were suspended in 35 mL of cold (−30° C.) toluene. To this mixture was added 0.98 mL of "3M diethyl ether solution of MeMgBr." The reaction mixture remained pale yellow for about 20 minutes, and then started to darken. After 1.5 hr of stifling, the solvent was removed under reduced pressure. To the residue was added 20 mL of toluene, followed by 25 mL of hexane. The suspension was filtered, giving a colorless solution. Solvent was removed under reduced pressure, giving 0.404 g of white solid. Yield 52%. Major Diastereomer: 1H NMR (400 MHz, C6D6) δ 8.30 (br s, 2H), 8.06 (br s, 2H), 7.53 (d, J=8 Hz, 2H), 7.43 (d, J=8 Hz, 2H), 7.34 (d, J=8 Hz, 2H), 7.30 (d, J=8 Hz, 2H), 7.24 (m, 4H), 7.19 (m, 4H), 6.34 (m, 1H), 6.21 (m, 1H), 4.50 (m, 2H), 3.30 (m, 1H), 1.71 (br s, 4H), 1.51 (br s, 18H), 1.36 (br s, 18H), 1.3-1.25 (m, 14H), 0.79 (s, 9H), 0.77 (s, 9H), 0.45 (d, J=3 Hz, 3H), −1.75 (s, 3H), −1.85 (s, 3H).

CAT 61-C3Et-Hf

The 6',6'''-(1-ethyl-propane-1,3-diylbis(oxy))bis(3-(3,6-di-tert-butyl-9H-carbazol-9-yl)-3'-fluoro-5-(2,4,4-trimethyl-pentan-2-yl)-[1,1'-biphenyl]-2-ol) (0.300 g, 0.24 mmol) and HfCl4 (0.077 g, 0.24 mmol) were suspended in 35 mL of cold (−30° C.) toluene. To this mixture was added 0.40 mL of "3M diethyl ether solution of MeMgBr." The reaction mixture remained pale yellow for about 20 minutes, and then started to darken. After 1.5 hr of stifling, the solvent was removed under reduced pressure. To the residue was added 20 mL of toluene, followed by 25 mL of hexane. The suspension was filtered, giving a colorless solution. Solvent was removed under reduced pressure, giving 0.423 g of white solid. Yield 57%. Major Diastereomer: 1H NMR (400 MHz, C6D6) δ 8.32 (d, J=4 Hz, 2H), 8.42 (d, J=4 Hz, 2H), 7.68 (d, J=8 Hz, 2H), 7.61 (d, J=8 Hz, 2H), 7.59 (d, J=8 Hz, 2H), 7.48 (d, J=8 Hz, 2H), 7.25 (m, 4H), 6.98 (m, 2H), 6.92 (m, 2H), 6.68 (m, 1H), 6.58 (m, 1H), 4.93 (m, 2H), 3.19 (m, 1H), 1.69 (br s, 4H), 1.51 (br s, 18H), 1.36 (br s, 18H), 1.3-1.25 (m, 14H), 0.85 (s, 9H), 0.83 (s, 9H), 0.32 (t, J=8 Hz, 3H), −0.95 (s, 3H), −1.05 (s, 3H).

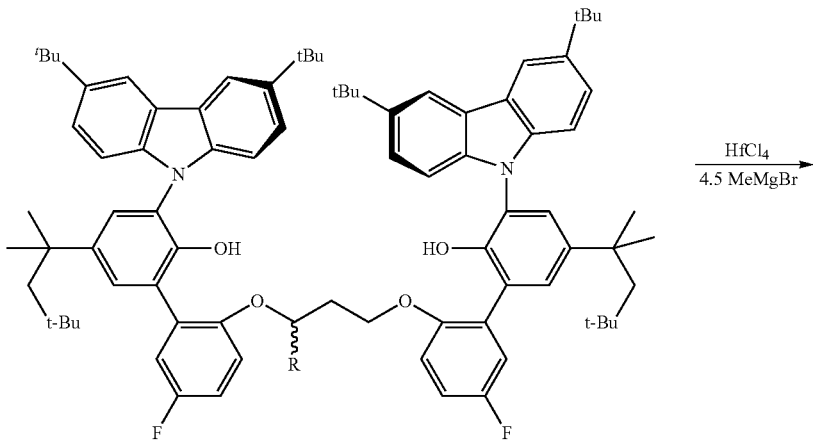

R = Me, Et

-continued

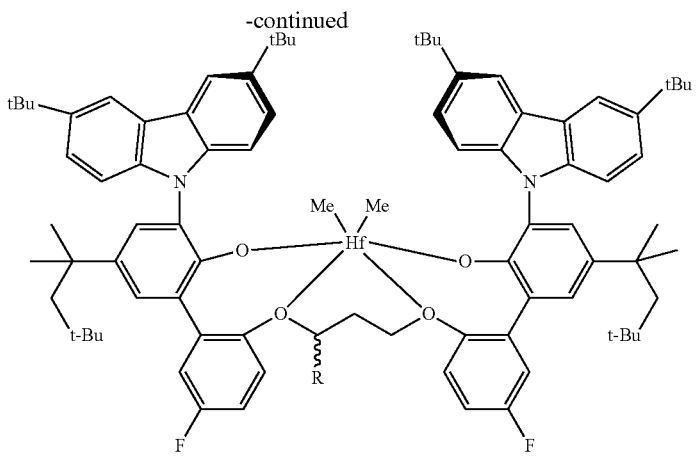

CAT 61-C3Me-Zr

The 6',6'''-(1-methyl-propane-1,3-diylbis(oxy))bis(3-(3,6-di-tert-butyl-9H-carbazol-9-yl)-3'-fluoro-5-(2,4,4-trimethyl-pentan-2-yl)-[1,1'-biphenyl]-2-ol) (0.350 g, 0.28 mmol) and ZrCl4 (0.066 g, 0.28 mmol) were suspended in 35 mL of cold (−30° C.) toluene. To this mixture was added 0.47 mL of "3M diethyl ether solution of MeMgBr." The reaction mixture remained pale yellow for about 20 minutes, and then started to darken. After 1.5 hr of stifling, the solvent was removed under reduced pressure. To the residue was added 20 mL of toluene, followed by 25 mL of hexane. The suspension was filtered, giving a colorless solution. Solvent was removed under reduced pressure, giving 0.315 g of white solid. Yield 82%. Major Diastereomer: 1H NMR (400 MHz, C6D6) δ 8.32 (br s, 2H), 8.04 (br s, 2H), 7.51 (d, J=8 Hz, 2H), 7.44 (d, J=8 Hz, 2H), 7.35 (d, J=8 Hz, 2H), 7.32 (d, J=8 Hz, 2H), 7.22 (m, 4H), 7.17 (m, 4H), 6.29 (m, 1H), 6.18 (m, 1H), 4.46 (m, 2H), 3.32 (m, 1H), 1.72 (br s, 4H), 1.52 (br s, 18H), 1.37 (br s, 18H), 1.3-1.24 (m, 14H), 0.80 (s, 9H), 0.78 (s, 9H), 0.44 (d, J=3 Hz, 3H), −1.02 (s, 3H), −1.34 (s, 3H).

CAT 61-C3Et-Zr

The 6',6'''-(1-ethyl-propane-1,3-diylbis(oxy))bis(3-(3,6-di-tert-butyl-9H-carbazol-9-yl)-3'-fluoro-5-(2,4,4-trimethyl-pentan-2-yl)-[1,1'-biphenyl]-2-ol) (0.350 g, 0.28 mmol) and ZrCl4 (0.065 g, 0.28 mmol) were suspended in 35 mL of cold (−30° C.) toluene. To this mixture was added 0.47 mL of "3M diethyl ether solution of MeMgBr." The reaction mixture remained pale yellow for about 20 minutes, and then started to darken. After 1.5 hr of stifling, the solvent was removed under reduced pressure. To the residue was added 20 mL of toluene, followed by 25 mL of hexane. The suspension was filtered, giving a colorless solution. Solvent was removed under reduced pressure, giving 0.333 g of white solid. Yield 88%. Major Diastereomer: 1H NMR (400 MHz, C6D6) δ 8.28 (d, J=4 Hz, 2H), 8.43 (d, J=4 Hz, 2H), 7.67 (d, J=8 Hz, 2H), 7.63 (d, J=8 Hz, 2H), 7.61 (d, J=8 Hz, 2H), 7.48 (d, J=8 Hz, 2H), 7.24 (m, 4H), 7.00 (m, 2H), 6.93 (m, 2H), 6.71 (m, 1H), 6.62 (m, 1H), 4.95 (m, 2H), 3.21 (m, 1H), 1.67 (br s, 4H), 1.50 (br s, 18H), 1.37 (br s, 18H), 1.31-1.26 (m, 14H), 0.86 (s, 9H), 0.84 (s, 9H), 0.34 (t, J=8 Hz, 3H), −0.78 (s, 3H), −0.92 (s, 3H).

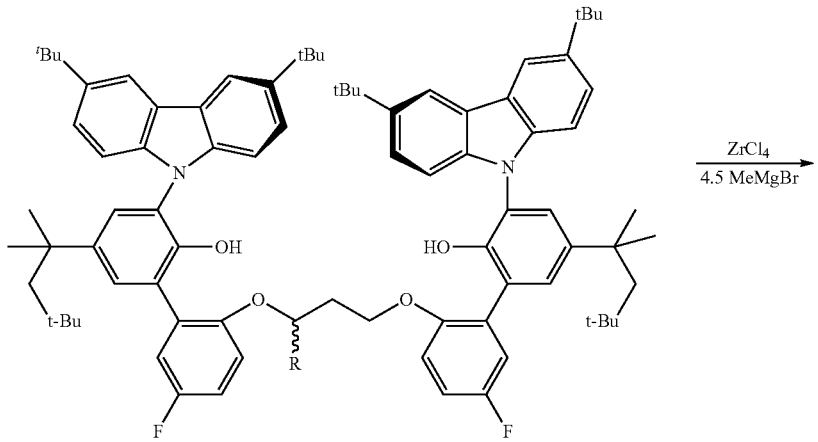

R = Me, Et

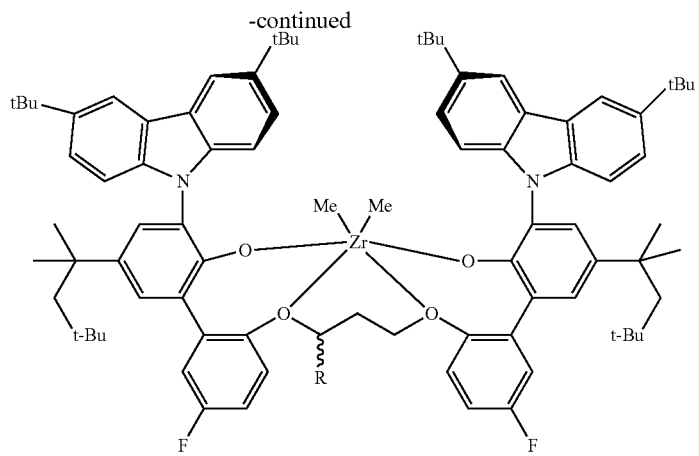

III. Polymerizations

Copolymers 1—Representative Polymerization

Each catalyst shown in Table 1 was used in a semi-batch reactor to produce ethylene/propylene copolymers or propylene/ethylene copolymers at 160° C. A one gallon, stirred autoclave reactor was charged with approximately 1.3 kg ISOPAR E mixed alkanes solvent and propylene (200 g). The reactor was heated to 160° C., and charged with hydrogen (20 mmol), followed by approximately 50 g of ethylene, to bring the total pressure up to approximately 430 psig. The ethylene feed was taken from the pilot plant feed, and passed through an additional purification column. The catalyst composition was prepared in a drybox, under inert atmosphere, by mixing the catalyst and cocatalyst mixture of 1.3 equiv bis(hydrogenated tallow alkyl)methyl amines and 100 equiv of triisobutylaluminum modified alumoxane (MMAO-3A), with additional solvent, to give a total volume of approximately 17 mL. The activated catalyst mixture was injected into the reactor over four minutes by a pump system. The reactor pressure and temperature were kept constant by feeding ethylene during the polymerization and cooling the reactor as needed. After 10 minutes, the ethylene feed was shut off, and the solution transferred into a nitrogen-purged resin kettle. An additive solution, containing a phosphorus stabilizer and phenolic antioxidant (IRGAFOS 168 and IGANOX 1010 in a 2:1 ratio by weight in toluene), was added, to give a total additive content of approximately 0.1 wt % in the polymer. The polymer was thoroughly dried in a vacuum oven. The reactor was thoroughly rinsed with hot hexanes between polymerizations.

Table 1 lists the polymer properties of the ethylene/propylene copolymers and propylene/ethylene copolymers prepared using the noted catalysts.

TABLE 1

Copolymers 1

| Catalyst | μmoles | Exotherm (° C.) | Yield (g) | Efficiency (gpoly/gmetal) | Mw | Mw/Mn | wt % C3 |
|---|---|---|---|---|---|---|---|
| CAT 61 (comparative) | 0.09 | 7.5 | 23 | 1,444,133 | 295,486 | 1.96 | 56.9 |
| CAT 61-C3Me | 0.44 | 7.6 | 19 | 244,461 | 471,807 | 2.28 | 53.6 |
| CAT 61-C3Et | 1.88 | 3.5 | 11 | 31,885 | 476,504 | 2.11 | 47.3 |
| CAT 54 (comparative) | 0.06 | 5.6 | 19 | 3,471,309 | 75,623 | 2.04 | 22.3 |
| CAT 61-C3Me—Zr | 0.25 | 5.7 | 22 | 964,658 | 125,176 | 2.15 | 21.5 |
| CAT 61-C3Et—Zr | 1.00 | 4.2 | 18 | 197,316 | 128,109 | 2.23 | 20.7 |

Copolymers 2—Representative Polymerization

Each catalyst shown in Table 2 was used in a semi-batch reactor to produce EP or PE polymers at 160° C. A one gallon, stirred autoclave reactor was charged with approximately 1.3 kg ISOPAR E mixed alkanes solvent and propylene (200 g). The reactor was heated to 160° C., and charged with hydrogen (20 mmol), followed by approximately 50 g of ethylene, to bring the total pressure up to approximately 430 psig. The ethylene feed was taken from the pilot plant feed, and passed through an additional purification column. The catalyst composition was prepared in a drybox, under inert atmosphere, by mixing the catalyst and cocatalyst (mixture of 1.3 equiv bis(hydrogenated tallow alkyl)methyl amines and 50 equiv of triisobutylaluminum modified alumoxane (MMAO-3A)), with additional solvent, to give a total volume of approximately 17 mL. The activated catalyst mixture was injected into the reactor over four minutes by a pump system. The reactor pressure and temperature were kept constant by feeding ethylene during the polymerization and cooling the reactor as needed. After 10 minutes, the ethylene feed was shut off, and the solution transferred into a nitrogen-purged resin kettle. An additive solution, containing a phosphorus stabilizer and phenolic antioxidant (IRGAFOS 168 and IGANOX 1010 in a 2:1 ratio by weight in toluene), was added, to give a total additive content of approximately 0.1 wt % in the polymer. The polymer was thoroughly dried in a vacuum oven. The reactor was thoroughly rinsed with hot hexanes between polymerizations.

Table 2 lists the polymer properties of the ethylene/propylene copolymers and the propylene/ethylene copolymer prepared using the noted catalysts.

TABLE 2

Copolymers 2

| Catalyst | μmoles | Exotherm (° C.) | Yield (g) | Efficiency (gpoly/gmetal) | Mw | Mw/Mn | wt % C3 |
|---|---|---|---|---|---|---|---|
| CAT 61 (comparative) | 0.5 | 6.8 | 175 | 1,960,784 | 306,862 | 2.84 | 53.1 |
| CAT 61-C3Me | 1.00 | 7.2 | 57 | 624,836 | 642,731 | 2.75 | 49.7 |
| CAT 54 (comparative) | 0.1 | 5.4 | 40 | 4,384,811 | 77,792 | 2.48 | 19.6 |
| CAT 61-C3Me—Zr | 0.8 | 5.2 | 33 | 452,183 | 155,412 | 2.56 | 18.3 |

Ethylene/Propylene/5-Ethylidene 2-Norbornene Terpolymers (EPDMs)—Representative Polymerization A one gallon, stirred autoclave reactor was charged with approximately 1.3 kg ISOPAR E mixed alkanes solvent, 12 g of 5-ethylidene 2-norbornene (ENB) and propylene (70 g). The reactor was heated to 175° C., and charged with hydrogen (20 mmol), followed by approximately 68 g of ethylene, to bring the total pressure up to approximately 430 psig. The ethylene feed was taken from the pilot plant feed, and passed through an additional purification column. The catalyst composition was prepared in a drybox, under inert atmosphere, by mixing the catalyst and cocatalyst (mixture of 1.2 equiv bis(hydrogenated tallow alkyl)methyl amines and 50 equiv of triisobutylaluminum modified alumoxane (MMAO-3A)), with additional solvent, to give a total volume of approximately 17 mL. The activated catalyst mixture was injected into the reactor over four minutes by a pump system. The reactor pressure and temperature were kept constant by feeding ethylene during the polymerization and cooling the reactor as needed. After 10 minutes, the ethylene feed was shut off, and the solution transferred into a nitrogen-purged resin kettle. An additive solution, containing a phosphorus stabilizer and phenolic antioxidant (IRGAFOS 168 and IGANOX 1010 in a 2:1 ratio by weight in toluene), was added, to give a total additive content of approximately 0.1 wt % in the polymer. The polymer was thoroughly dried in a vacuum oven. The reactor was thoroughly rinsed with hot hexanes between polymerizations.

Table 3 lists the polymer properties of the EPDMs prepared using the noted catalysts.

Ethylene/Octene Copolymers 1 (140° C.)—Representative Polymerization

A one gallon, stirred autoclave reactor was charged with approximately 1.3 kg ISOPAR E mixed alkanes solvent and 1-octene (251 g). The reactor was heated to 140° C., and charged with hydrogen (20 mmol), followed by approximately 95 g of ethylene, to bring the total pressure up to approximately 430 psig. The ethylene feed was taken from the pilot plant feed, and passed through an additional purification column. The catalyst composition was prepared in a drybox, under inert atmosphere, by mixing the catalyst and cocatalyst (mixture of 1.3 equiv bis(hydrogenated tallow alkyl)methyl amines and 50 equiv of triisobutylaluminum modified alumoxane (MMAO-3A), with additional solvent, to give a total volume of approximately 17 mL. The activated catalyst mixture was injected into the reactor over four minutes by a pump system. The reactor pressure and temperature were kept constant by feeding ethylene during the polymerization and cooling the reactor as needed. After 10 minutes, the ethylene feed was shut off, and the solution transferred into a nitrogen-purged resin kettle. An additive solution containing a phosphorus stabilizer and phenolic antioxidant (IRGAFOS 168 and IGANOX 1010 in a 2:1 ratio by weight in toluene), was added, to give a total additive content of approximately 0.1 wt % in the polymer. The polymer was thoroughly dried in a vacuum oven. The reactor was thoroughly rinsed with hot hexanes between polymerizations.

Table 4 lists the polymer properties of the ethylene/octene copolymers prepared using the noted catalysts.

TABLE 3

EPDMs

| Catalyst | μmoles | Exotherm (° C.) | Yield (g) | Efficiency (gpoly/gmetal) | Mw | Mw/Mn | wt % C3 | Wt % ENB |
|---|---|---|---|---|---|---|---|---|
| CAT 61 (comparative) | 0.15 | 6.2 | 30 | 1,120,510 | 275,368 | 2.12 | 25.2 | 4.7 |
| CAT 61-C3Me | 0.18 | 5.1 | 17 | 529,130 | 352,562 | 2.21 | 22.3 | 4.8 |
| CAT 54 (comparative) | 0.10 | 4.9 | 25 | 2,740,506 | 56,032 | 2.10 | 13.1 | 2.5 |
| CAT 61-C3Me—Zr | 0.25 | 5.2 | 21 | 920,810 | 101,309 | 2.32 | 12.7 | 2.7 |

TABLE 4

| | | EO Copolymers 1 (140° C.) | | | | | |
|---|---|---|---|---|---|---|---|
| Catalyst | μmoles | Exotherm (° C.) | Yield (g) | Efficiency (gpoly/gmetal) | Mw | Mw/Mn | wt % C8 |
| CAT 61 (comparative) | 0.07 | 5.7 | 19 | 1,520,693 | 223,982 | 2.08 | 32.3 |
| CAT 61-C3Me | 0.15 | 5.0 | 19 | 709,656 | 301,230 | 2.19 | 31.0 |
| CAT 54 (comparative) | 0.05 | 6.0 | 25 | 5,481,013 | 66,981 | 2.06 | 15.6 |
| CAT 61-C3Me—Zr | 0.10 | 5.1 | 21 | 2,302,025 | 105,671 | 2.18 | 13.4 |

Ethylene/Octene Copolymers 2 (190° C.)—Representative Polymerization

A one gallon stirred autoclave reactor was charged with approximately 1.3 kg ISOPAR E mixed alkanes solvent and 1-octene (251 g). The reactor was heated to 190° C., and charged with hydrogen (20 mmol), followed by approximately 95 g of ethylene, to bring the total pressure up to approximately 430 psig. The ethylene feed was taken from the pilot plant feed, and passed through an additional purification column. The catalyst composition was prepared in a drybox, under inert atmosphere, by mixing the catalyst and cocatalyst (mixture of 1.3 equiv bis(hydrogenated tallow alkyl)methyl amines and 50 equiv of triisobutylaluminum modified alumoxane (MMAO-3A)), with additional solvent, to give a total volume of approximately 17 mL. The activated catalyst mixture was injected into the reactor over four minutes by a pump system. The reactor pressure and temperature were kept constant by feeding ethylene during the polymerization and cooling the reactor as needed. After 10 minutes, the ethylene feed was shut off, and the solution transferred into a nitrogen-purged resin kettle. An additive solution, containing a phosphorus stabilizer and phenolic antioxidant (IRGAFOS 168 and IGANOX 1010 in a 2:1 ratio by weight in toluene), was added, to give a total additive content of approximately 0.1 wt % in the polymer. The polymer was thoroughly dried in a vacuum oven. The reactor was thoroughly rinsed with hot hexanes between polymerizations.

Table 5 lists the polymer properties of the ethylene/octene copolymers prepared using the noted catalysts.

TABLE 5

| | | EO Copolymers 2 (190° C.) | | | | | |
|---|---|---|---|---|---|---|---|
| Catalyst | μmoles | Exotherm (° C.) | Yield (g) | Efficiency (gpoly/gmetal) | Mw | Mw/Mn | wt % C8 |
| CAT 61 (comparative) | 0.09 | 6.2 | 18 | 1,120,510 | 145,440 | 2.09 | 29.6 |
| CAT 61-C3Me | 0.25 | 6.0 | 21 | 470,614 | 203,451 | 2.23 | 28.0 |
| CAT 54 (comparative) | 0.06 | 5.8 | 22 | 4,019,410 | 35,672 | 2.05 | 14.3 |
| CAT 61-C3Me—Zr | 0.20 | 5.2 | 19 | 1,041,392 | 67,982 | 2.18 | 12.8 |

Summary Of Results

As shown by the above inventive polymerizations, the inventive catalysts effectively polymerize ethylene with alpha-olefins, and ethylene with alpha-olefins and diene. The inventive polymerizations can be run at high polymerization temperatures, and yield ethylene-based polymers with high molecular weights. The inventive catalysts also show high catalytic activity at the high reaction temperatures.

The invention claimed is:

1. A process to form an ethylene-based polymer, said process comprising at least the following:
polymerizing ethylene in the presence of a metal complex selected from Structure I below:

(Structure I)

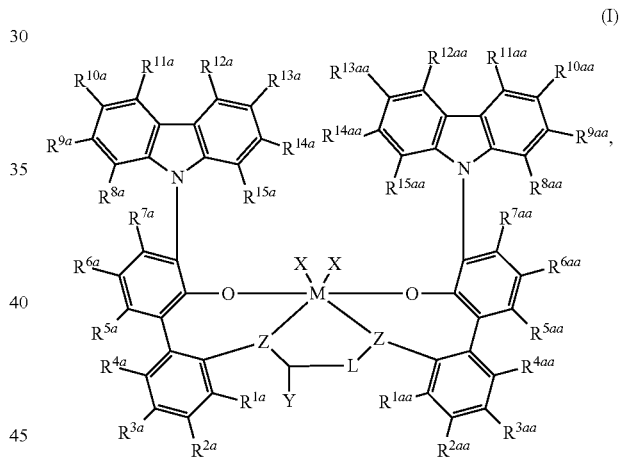

(I)

wherein:
M is a metal selected from Group 3, Group 4, Group 5 or Group 6 of the Periodic Table of the Elements;
R1a, R1aa, R2a, R2aa, R3a, R3aa, R4a, R4aa, R5a, R5aa, R6a, R6aa, R7a, R7aa, R8a, R8aa, R9a, R9aa, R10a, R10aa, R11a, R11aa, R12a, R12aa, R13a, R13aa, R14a, R14aa, R15a, R15aa, independently in each occurrence, is hydrogen, halo, hydrocarbyl, trihydrocarbylsilyl, trihydrocarbylsilylhydrocarbyl, —O(R), —N(R'R''), —S(R'''), or —P($R^{IV}R^{V}$); and wherein each R, R', R'', R''', $R^{IV}$ and $R^{V}$ is independently hydrogen, a C1-C18 aliphatic hydrocarbyl, or a C1-C18 heterohydrocarbyl;

each X is independently selected from halo, hydrocarbyl, or trihydrocarbylsilyl group;

each Z is independently selected from O, S, N(C1-C40) hydrocarbyl, or P(C1-C40)hydrocarbyl;

Y is selected from halo, hydrocarbyl, trihydrocarbylsilyl, trihydrocarbylsilyl-hydrocarbyl, —O($R^{VI}$), —N($R^{VII}R^{VIII}$), —S($R^{IX}$), or —P($R^{X}R^{XI}$); and wherein each $R^{VI}$, $R^{VII}$, $R^{VIII}$, $R^{IX}$, $R^{X}$ and $R^{XI}$ is independently hydrogen, a C1-C18 aliphatic hydrocarbyl or a C1-C18 heterohydrocarbyl;

L is —CH$_2$CH$_2$CH$_2$.

2. The process of claim 1, wherein each Z is O.

3. The process of claim 1, wherein R6a and R6aa are each independently a (C$_4$-C$_{40}$)hydrocarbyl.

4. The process of claim 1, wherein R10a, R13a, R10aa and R13aa are each independently a (C$_1$-C$_{40}$)hydrocarbyl.

5. The process of claim 1, wherein R3a and R3aa are each independently a (C$_1$-C$_6$)alkyl, a (C$_1$-C$_6$)alkyl-O—, a ((C$_1$-C$_6$)alkyl)$_2$-N—, a (C$_3$-C$_6$)cycloalkyl, a fluorine atom, or a chlorine atom.

6. The process of claim 1, wherein R3a, R3aa, R10a, R13a, R10aa, R13aa, R6a and R6aa are not hydrogen atoms; and R3a and R3aa are the same as each other; R6a and R6aa are the same as each other; and R10a and R13a are respectively the same as R10aa and R13aa.

7. The process of claim 1, wherein the metal (M) is hafnium, zirconium, or titanium.

8. A process to form an ethylene-based polymer, said process comprising at least the following: polymerizing ethylene in the presence of a metal complex selected from the following Structure II:

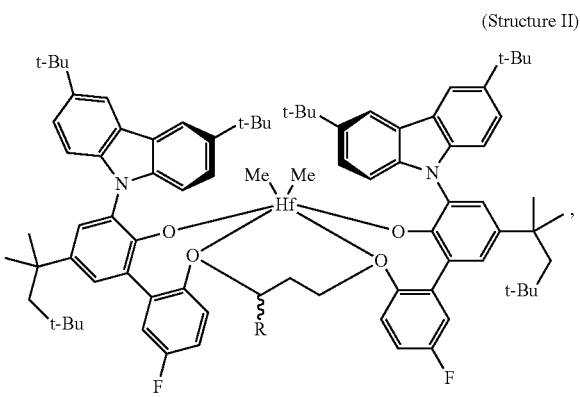

(Structure II)

wherein R is a (C1-C8) alkyl group.

9. The process of claim 8, wherein, for Structure II, wherein R is selected from methyl, ethyl, n-propyl, iso-propyl, n-butyl, iso-butyl, or tert-butyl.

10. A metal complex selected from the following Structure II:

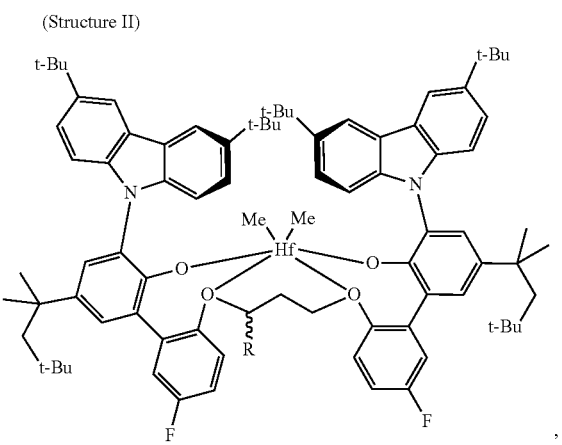

(Structure II)

wherein R is a (C1-C8) alkyl group.

* * * * *